United States Patent [19]

Mues et al.

[11] 4,247,560
[45] Jan. 27, 1981

[54] 6,7-METHYLENEDIOXY-ISOCHROMANE ARTHROPODICIDE SYNERGIZING AGENTS

[75] Inventors: Volker Mues, Wuppertal; Wolfgang Behrenz, Overath, both of Fed. Rep. of Germany

[73] Assignee: Bayer Aktiengesellschaft, Leverkusen, Fed. Rep. of Germany

[21] Appl. No.: 24,746

[22] Filed: Mar. 28, 1979

[30] Foreign Application Priority Data

Apr. 15, 1978 [DE] Fed. Rep. of Germany ....... 2816475

[51] Int. Cl.$^2$ ...................... A01N 9/28; C07D 317/44
[52] U.S. Cl. .............................. 424/282; 260/340.5 R
[58] Field of Search .................. 260/340.5 R; 424/282

[56] References Cited

U.S. PATENT DOCUMENTS 3,954,991  5/1976  Stevens et al. .................... 260/340.5
4,098,799  7/1978  Klutchko et al. ............... 424/282 X

OTHER PUBLICATIONS

Srivastava et al., Journ. Org. Chem., vol. 27 (1962), pp. 4337–4341.

Primary Examiner—Ethel G. Love
Attorney, Agent, or Firm—Sprung, Felfe, Horn, Lynch & Kramer

[57] ABSTRACT 6,7-Methylenedioxy-isochromanes of the formula

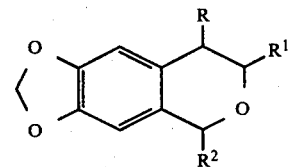

in which R, $R^1$ and $R^2$ each independently is hydrogen or alkyl, which synergize with known arthropodicides.

4 Claims, No Drawings

6,7-METHYLENEDIOXY-ISOCHROMANE ARTHROPODICIDE SYNERGIZING AGENTS

The present invention relates to and has for its objects the provision of particular new 6,7-methylenedioxyisochromanes which synergize with known compounds of known arthropodicidal activity, active composition in the form of synergistic mixtures of such compounds optionally with solid and liquid dispersible carrier vehicles, and methods for producing such compounds and for using such compounds in a new way especially for combating pests, e.g. insects, and acarids, with other and further objects becoming apparent from a study of the within specification and accompanying examples.

The invention relates to certain new isochromane derivatives, to a process for their preparation and to their use as synergistic agents in arthropodicidal, especially insecticidal and acaricidal, compositions.

It is already known that the following active compounds or groups of active compounds possess pesticidal, especially insecticidal and acaricidal, properties:

(A) carbamates, for example 2-iso-propoxy-phenyl N-methylcarbamate, 3,4,5-trimethyl-phenyl N-methylcarbamate, 1-naphthyl N-methyl-carbamate, 2,3-dihydro-2,2-dimethyl-7-benzofuranyl N-methyl-carbamate, 2-(1,3-dioxolan-2-yl-phenyl) N-methyl-carbamate and 2,2-dimethyl-1,3-benzodioxol-4-yl N-methyl carbamate, (B) carboxylic acid esters, for example 2,3,4,5-tetrahydro-phthalimido-methyl chrysanthemate and (5-benzyl-3-furyl)-methyl 2,2-dimethyl-3-(2-methyl-propenyl)-cyclo-propane-carboxylate, (C) phosphoric acid esters, for example O,O-dimethyl-O-(2,2-dichlorovinyl)-phosphoric acid ester and (D) halogenoalkanes, for example 1,1,1-trichloro-2,2-bis-(4-methoxyphenyl)-ethane and 1,1,1-trichloro-2,2-bis-(4-chlorophenyl)-ethane.

In addition, synergistic mixtures of carbamates, for example 2-iso-propoxy-phenyl N-methylcarbamate, or of phosphoric acid esters, for example O,O-diethyl-O-(2-iso-propyl-4-methylpyrimidin-6-yl)-thionophosphoric acid ester, or of natural or synthetic pyrethroids, with piperonyl ethers, for example α-(2-(2-butoxy-ethoxy)-ethoxy)-4,5-methylenedioxy-2-propyl-toluene, are known (see Bull. Org. mond. Sante/Bull. Wld.Hlth Org. 1966, 35 691–708; and Schrader, G., Die Entwicklung neuer insektizider Phosphorsäureester (The Development of New Insecticidal Phosphoric Acid Esters), 1963, page 158). However, the activity of these synergistic active compound combinations is not satisfactory. Hitherto, only α-(2-(2-butoxy-ethoxy)-ethoxy)-4,5-methylenedioxy-2-propyl-toluene has attained some practical importance.

The present invention now provides, as new compounds, the isochromane derivatives of the general formula

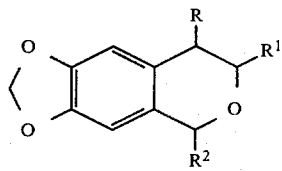

in which R, $R^1$ and $R^2$, independently of one another, each represent hydrogen or alkyl.

Preferably, R, $R^1$ and $R^2$, independently of one another, each represent hydrogen or straight-chain or branched alkyl with 1 to 5 (especially 1 to 3) carbon atoms.

The invention also provides a process for the preparation of an isochromane derivative of the formula (I) in which a benzodioxole derivative of the general formula

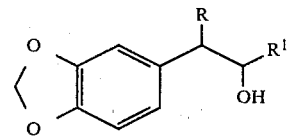

in which R and $R^1$ have the above-mentioned meanings, is reacted with an aldehyde of the general formula

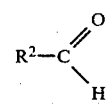

in which $R^2$ has the above-mentioned meaning, if appropriate in the presence of a catalyst and, if appropriate, in the presence of a diluent.

The invention also provides an arthropodicidal composition containing as active ingredients (1) at least one isochromane derivative of the formula (I) and (2) at least one compound selected from (A) carbamates, (B) carboxylic acid esters (including the natural and synthetic pyrethrods), (C) phosphoric acid esters and (D) halogenoalkanes, alone or in admixture with a diluent or carrier.

The invention also provides a method of combating arthropods, especially insects or acarids, which comprises applying to the arthropods, or to a habitat thereof, a composition according to this invention.

The synergistic action of the compounds of the general formula (I) manifests itself preferentially with compounds of certain preferred classes.

Preferred carbamates (A) are those of the general formula

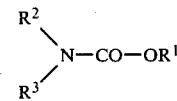

in which $R^1$ represents aryl, a heterocyclic ring or an oxime radical, $R^2$ represents hydrogen or an alkyl radical with 1 to 4 carbon atoms and $R^3$ represents alkyl, alkylcarbonyl with 1 to 6 carbon atoms in the alkyl radical, which optionally can also be substituted by hydroxyl or methylthio, or the radical —S—Z, wherein Z represents an optionally halogen-substituted aliphatic radical with 1 to 4 carbon atoms (especially $CCl_3$ and $CF_3$), an optionally substituted aryl radical (especially phenyl) (preferred substituents being nitrile, halogen, especially chlorine, methyl, trihalogenomethyl, trifluoromethylmercapto or nitro), methoxycarbonyl or the radical

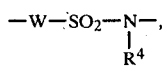

wherein

W represents alkyl, halogenoalkyl, alkylamino, dialkylamino or an optionally substituted aryl radical (preferred substituents being halogen, trihalogenomethyl, nitrile, methyl or nitro).

Particularly preferred carbamates of the formula (II) are those wherein $R^1$ represents phenyl or naphthyl, which are optionally substituted by alkyl, alkenyl, alkoxy, alkylmercapto or alkylthioalkyl, in each case with 1 to 6 carbon atoms, dialkylamino and dialkenylamino, with up to 3 carbon atoms per alkyl or alkenyl part, halogen, especially chlorine, dioxolanyl or the $—N=CH—N(C_{1-4}\text{-}alkyl)_2$ radical, or wherein $R^1$ represents 2,3-dihydrobenzofuranyl, benzodioxole, benzothienyl, pyrimidinyl or pyrazolyl, which are optionally substituted by alkyl with 1 to 4 carbon atoms (especially methyl) and/or dialkylamino with 1 to 4 carbon atoms per alkyl part, or wherein $R^1$ represents a radical of the general formula

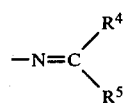

(IIa)

in which $R^4$ and $R^5$, which may be identical or different, each represent alkyl, cycloalkyl, alkenyl, alkynyl, alkoxy, alkylmercapto, alkoxycarbonyl, amidocarbonyl, or alkylmercaptoalkyl, in each case with up to 5 carbon atoms, nitrile, aryl (especially phenyl), or $R^4$ and $R^5$ conjointly represent a dioxolanyl or dithiolanyl radical which is optionally substituted by $C_{1-4}$-alkyl.

The following carbamates of the formula (II) may be mentioned specifically: 2-methylphenyl, 2-ethylphenyl, 2-n-propylphenyl, 2-methoxyphenyl, 2-ethoxyphenyl, 2-isopropoxyphenyl, 4-methylphenyl, 4-ethylphenyl, 4-n-propylphenyl, 4-methoxyphenyl, 4-ethoxyphenyl, 4-n-propoxyphenyl, 3,4,5-trimethylphenyl, 1-naphthyl, 2,3-dihydro-2,2-dimethyl-7-benzofuranyl, 2-(1,3-dioxolan-2-yl-phenyl) and 2,2-dimethyl-1,3-benzodioxol-4-yl N-methyl-carbamate and the corresponding N-methyl-N-acetyl-, N-methyl-N-trifluoromethylthio-, N-methyl-N-dichloromonofluoromethylthio- and N-methyl-N-dimethylaminothio-carbamates.

Preferred carboxylic acid esters (B) are those of the general formula

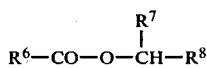

(III)

in which $R^6$ represents alkyl, aralkyl, aryl or cycloalkyl, any of which can optionally be substituted, $R^7$ represents hydrogen, alkyl, halogenoalkyl, alkenyl, alkynyl or nitrile and $R^8$ represents aryl or a heterocylic ring, or conjointly with $R^7$ forms an optionally substituted cyclopentenone ring.

Particularly preferred carboxylic acid esters of the formula (III) are those in which $R^6$ represents alkyl with 1 to 6 carbon atoms, which is optionally substituted by optionally halogen-substituted phenyl, or represents cyclopropyl, which is optionally substituted by alkyl, alkenyl, halogenoalkyl or halogenoalkenyl, each with up to 6 carbon atoms, or represents phenyl, which is optionally substituted by halogen, $R^7$ represents hydrogen, alkyl with 1 to 6 carbon atoms, halogenoalkyl with 1 to 4 carbon atoms and up to 3 halogen atoms, nitrile or ethynyl, $R^8$ represents phenyl which is optionally substituted by $C_{1-4}$-alkyl, halogen, especially fluorine or chlorine, or optionally halogen-substituted or methyl-substituted phenoxy or optionally substituted benzyl, or represents furanyl, tetrahydrophthalimido, or benzodioxole, which are optionally substituted by halogen, especially fluorine, alkyl or alkenyl with up to 4 carbon atoms, or benzyl, or together with $R^7$ and the CH moiety represents cyclopentenone, which is optionally substituted by $C_{1-4}$-alkyl, furfuryl or $C_{1-5}$-alkenyl.

The following may be mentioned specifically: 1-(3,4-dichlorophenyl)-2,2,2-trichloroethyl acetate, 2,3,4,5-tetrahydrophthalimidomethyl chrysanthemate and (5-benzyl-3-furyl)methyl 2,2-dimethyl-3-(2-methyl-propenyl)-cyclopropanecarboxylate. In addition, the naturally occurring pyrethroids are also particularly preferred.

Preferred phosphoric acid esters (C) are those of the general formula

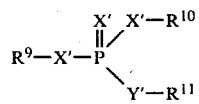

(IV)

in which each $X'$ independently of the others represents O or S, $Y'$ represents O, S, —NH— or a direct bond between the central P atom and $R^{11}$, and $R^9$ and $R^{10}$, which may be identical or different, each represent alkyl or aryl, and $R^{11}$ represents alkyl, aryl, heteroaryl, aralkyl, alkenyl, dioxanyl or an oxime radical or a radical identical to that to which it is bonded.

Particularly preferred phosphoric acid esters (IV) are those in which $R^9$ and $R^{10}$, which may be identical or different, each represent $C_{1-4}$-alkyl or phenyl, and $R^{11}$ represents alkyl with 1 to 4 carbon atoms, which is optionally substituted by halogen, hydroxyl, nitrile, optionally halogen-substituted phenyl, amidocarbonyl, $C_{1-4}$-alkylamidocarbonyl, sulphonyl-$C_{1-4}$-alkyl, sulphoxy-$C_{1-4}$-alkyl, carbonyl-$C_{1-4}$-alkyl, $C_{1-4}$-alkoxy, $C_{1-4}$-alkylmercapto or $C_{1-4}$-alkoxy-carbonyl, or represents alkenyl with up to 4 carbon atoms, which is optionally substituted by halogen, optionally halogen-substituted phenyl or alkoxy-carbonyl, or represents an oxime radical of the general formula

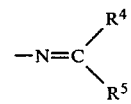

(IIa)

wherein $R^4$ and $R^5$ have the above-mentioned meanings, but preferably represent cyano or phenyl, or $R^{11}$ represents dioxanyl which is substituted by a radical identical to that to which $R^{11}$ is bonded, or $R^{11}$ represents a radical identical to that to which it is bonded, or $R^{11}$ represents phenyl which is optionally substituted by methyl, nitro, nitrile, halogen or methylthio, or, particularly preferentially, $R^{11}$ represents an optionally $C_{1-4}$-alkyl-substituted or halogen-substituted hetero-aromatic, such as pyridine, quinoline, quinoxaline, pyrimidine, diazinone or benzo-1,2,4-triazine.

The following may be mentioned specifically: O,O-dimethyl- and O,O-diethyl-O-(2,2-dichloro- or 2,2-dibromo-vinyl)phosphoric acid ester, O,O-diethyl-O-(4-nitro-phenyl)thionophosphoric acid ester, O,O-dimethyl-O-(3-methyl-4-methylthio)-thionophosphoric acid ester, O,O-dimethyl-O-(3-methyl-4-nitro)-thionophosphoric acid ester, O-ethyl-S-n-propyl-O-(2,4-dichlorophenyl)-thionophosphoric acid ester, O-ethyl-S-n-propyl-O-(4-methylthio-phenyl)-thionophosphoric acid ester, O,O-dimethyl-S-(4-oxo-1,2,3-benzotriazin-3-yl-methyl)-thionothiolphosphoric acid ester, O-methyl-O-(2-iso-propyl-6-methoxy-pyrimidin-4-yl)-thionomethanephosphonic acid ester, O,O-diethyl-O-(2-iso-propyl-6-methyl-pyrimidin-4-yl)-thionophosphoric acid ester, O,O-diethyl-O-(3-chloro-4-methyl-coumarin-7-yl)-thionophosphoric acid ester, O,O-dimethyl-2,2,2-trichloro-hydroxy-ethane-phosphonic acid ester and O,O-dimethyl-S-(methylcarbamoylmethyl)-thionophosphoric acid ester.

Preferred halogenoalkanes (D) are those of the general formula

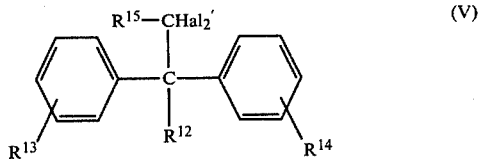

(V)

in which
Hal' represents chlorine or bromine and
$R^{12}$ represents hydrogen or hydroxyl,
$R^{13}$ and $R^{14}$, which may be identical or different, each represent halogen, alkyl or alkoxy and
$R^{15}$ represents hydrogen or halogen.

Particularly preferred halogenoalkanes (V) are those in which
$R^{12}$ represents hydrogen or hydroxyl,
$R^{13}$ and $R^{14}$ are identical and represent halogen, alkyl with 1 to 4 carbon atoms or alkoxy with 1 to 4 carbon atoms and
$R^{15}$ represents halogen.

The following may be mentioned specifically: 1,1,1-trichloro-2,2-bis(4-chloro- or 4-methoxy-phenyl)-ethane, 1,1,1-trichloro-2-hydroxy-2,2-bis(4-chlorophenyl)-ethane and 1,1-dichloro-2,2-bis(4-ethylphenyl)-ethane.

Surprisingly, the insecticidal and/or acaricidal action of the active compound combinations according to the invention is substantially greater than the action of the individual components and greater than the sum of the actions of the individual components. Furthermore, it is substantially greater than the action of the previously known active compound combination of 2-iso-propoxyphenyl N-methyl-carbamate and piperonyl butoxide. In addition, the isochromane derivatives which can be used according to the invention exhibit an excellent synergistic activity, not only with one class of active compounds, but with active compounds from a great variety of groups of chemical compounds.

Accordingly, the isochromane derivatives according to the invention, and the synergistic mixtures containing these derivatives, represent a valuable enrichment of the art.

The following may be mentioned as examples of the compounds of the formula (I): 6,7-methylenedioxy-isochromane, 1-methyl-, 1-ethyl-, 1-n-propyl-, 1-iso-propyl-, 3-methyl-, 3-ethyl-, 3-n-propyl-, 3-iso-propyl-, 4-methyl-, 4-ethyl-, 4-n-propyl-, 4-iso-propyl-, 1,3-dimethyl-, 1,3-diethyl-, 1,3-di-n-propyl-, 1,3-di-iso-propyl-, 1,4-dimethyl-, 1,4-diethyl-, 1,4-di-n-propyl-, 1,4-di-iso-propyl-, 3,4-dimethyl-, 3,4-diethyl-, 3,4-di-n-propyl-, 1-methyl-3-ethyl-, 1-methyl-3-n-propyl-, 1-methyl-3-iso-propyl-, 1-methyl-4-ethyl-, 1-methyl-4-n-propyl-, 1-methyl-4-iso-propyl-, 3-methyl-4-ethyl-, 3-methyl-4-n-propyl-, 3-methyl-4-iso-propyl-, 1-ethyl-3-methyl-, 1-ethyl-3-n-propyl-, 1-ethyl-3-iso-propyl-, 1-ethyl-4-methyl-, 1-ethyl-4-n-propyl-, 1-ethyl-4-iso-propyl-, 3-ethyl-4-methyl-, 3-ethyl-4-n-propyl-, 3-ethyl-4-iso-propyl-, 1-n-propyl-3-methyl-, 1-n-propyl-3-ethyl-, 1-n-propyl-3-iso-propyl-, 1-n-propyl-4-methyl-, 1-n-propyl-4-ethyl-, 1-n-propyl-4-iso-propyl-, 3-n-propyl-4-methyl-, 3-n-propyl-4-ethyl-, 3-n-propyl-4-iso-propyl-, 1-iso-propyl-3-methyl-, 1-iso-propyl-3-ethyl-, 1-iso-propyl-3-n-propyl-, 1-iso-propyl-4-methyl-, 1-iso-propyl-4-ethyl-, 1-iso-propyl-4-n-propyl-, 3-iso-propyl-4-methyl-, 3-iso-propyl-4-ethyl-, 3-iso-propyl-4-n-propyl-, 1,3,4-trimethyl-, 1,3,4-triethyl-, 1,3,4-tri-n-propyl-, 1-ethyl-3,4-dimethyl-, 1-n-propyl-3,4-dimethyl-, 1-iso-propyl-3,4-dimethyl-, 1-methyl-3,4-diethyl-, 1-n-propyl-3,4-diethyl-, 1-iso-propyl-3,4-di-n-propyl-, 1-sio-propyl-3,4-diethyl-, 1-methyl-3,4-di-n-propyl-, 1-ethyl-3,4-di-n-propyl-, 1,3-dimethyl-4-ethyl-, 1,3-dimethyl-4-n-propyl-, 1,3-dimethyl-4-iso-propyl-, 1,3-diethyl-4-methyl-, 1,3-diethyl-4-n-propyl-, 1,3-diethyl-4-iso-propyl-, 1,3-di-n-propyl-4-methyl-, 1,3-di-n-propyl-4-ethyl-, 1,3-di-n-propyl-4-iso-propyl-, 1,3-di-iso-propyl-4-methyl-, 1,3-di-iso-propyl-4-ethyl-, 1,3-di-iso-propyl-4-n-propyl-, 1,4-dimethyl-3-ethyl-, 1,4-dimethyl-3-n-propyl-, 1,4-dimethyl-3-iso-propyl-, 1,4-diethy-3-methyl-, 1,4-diethy-3-n-propyl-, 1,4-diethyl-3-iso-propyl-, 1,4-di-n-propyl-3-methyl-, 1,4-di-n-propyl-3-ethyl-, 1,4-di-n-propyl-3-iso-propyl-, 1,4-di-iso-propyl-3-methyl-, 1,4-di-iso-propyl-3-ethyl-, 1,4-di-iso-propyl-3-n-propyl-, 3,4-dimethyl-1-ethyl-, 3,4-di-methyl-1-n-propyl-, 3,4-dimethyl-1-iso-propyl-, 3,4-diethyl-1-methyl-, 3,4-diethyl-1-n-propyl-, 3,4-diethyl-1-iso-propyl-, 3,4-di-n-propyl-1-methyl-, 3,4-di-n-propyl-1-ethyl-, 1-methyl-3-ethyl-4-n-propyl-, 1-methyl-3-ethyl-4-iso-propyl-, 1-methyl-3-n-propyl-4-ethyl-, 1-methyl-3-n-propyl-4-iso-propyl-, 1-methyl-3-iso-propyl-4-ethyl-, 1-methyl-3-iso-propyl-4-n-propyl-, 1-ethyl-3-methyl-4-n-propyl-, 1-ethyl-3-methyl-4-iso-propyl-, 1-ethyl-3-n-propyl-4-methyl-, 1-ethyl-3-n-propyl-4-iso-propyl-, 1-ethyl-3-iso-propyl-4-methyl-, 1-ethyl-3-iso-propyl-4-n-propyl-, 1-n-propyl-3-methyl-4-iso-propyl-, 1-n-propyl-3-methyl-4-ethyl-, 1-n-propyl-3-ethyl-4-iso-propyl-, 1-n-propyl-3-ethyl-4-methyl-, 1-n-propyl-3-iso-propyl-4-methyl-, 1-n-propyl-3-iso-propyl-4-ethyl-, 1-iso-propyl-3-methyl-4-ethyl-, 1-iso-propyl-3-methyl-4-n-propyl-, 1-iso-propyl-3-ethyl-4-methyl-, 1-iso-propyl-3-ethyl-4-n-propyl-, 1-iso-propyl-3-n-propyl-4-methyl- and 1-iso-propyl-3-n-propyl-4-ethyl-6,7-methylenedioxy-isochromane.

The benzodioxole derivatives to be used as starting materials are defined by the formula (Ia). The following may be mentioned as examples: 4-(2-hydroxy-ethyl)-, 4-(2-hydroxy-n-propyl)-, 4-(2-hydroxy-n-butyl)-, 4-(2-hydroxy-n-pentyl)-, 4-(2-hydroxy-iso-pentyl)-, 4-(1-methyl-2-hydroxyethyl)-, 4-(1-ethyl-2-hydroxy-ethyl)-, 4-(1-n-propyl-2-hydroxy-ethyl)-, 4-(1-iso-propyl-2-hydroxy-ethyl)-, 4-(1-methyl-2-hydroxy-n-propyl)-, 4-(1-ethyl-2-hydroxy-n-propyl)-, 4-(1-n-propyl-2-hydroxy-n-propyl)-, 4-(1-iso-propyl-2-hydroxy-n-propyl)-, 4-(1-methyl-2-hydroxy-n-butyl)-, 4-(1-ethyl-2-hydroxy-n-butyl)-, 4-(1-n-propyl-2-hydroxy-n-butyl)-, 4-(1-iso-propyl-2-hydroxy-n-butyl)-, 4-(1-methyl-2-hydroxy-n-pentyl)-, 4-(1-ethyl-2-hydroxy-n-pentyl)-, 4-(1-n-propyl-2-hydroxy-n-pentyl)-, 4-(1-iso-propyl-2-hydroxy-n-pentyl)-, 4-(1-methyl-2-hydroxy-iso-pentyl)-, 4-(1-ethyl-2-hydroxy-iso-pentyl)- and 4-(1-n-propyl-2-hydroxy-iso-pentyl)-1,2-methylenedioxy-benzene.

Benzodioxole derivatives of the formula (Ia) are known (see DT-OS (German Published Specification) No. 2,624,693). They can be prepared if, for example, known compounds of the formula

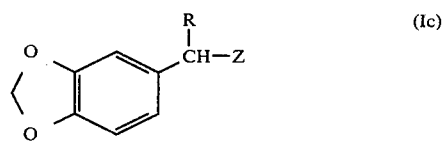

wherein
R has the above-mentioned meaning and
Z represents $COR^1$, $COOR^1$, or CN, with $R^1$ having the above-mentioned meaning,
are reduced in accordance with known methods. (See Ber. Deutsch. Chem. Ges. 41 (1908) pages 2,751–2,761).

In a special case (R=H; $R^1$=CH$_3$), isosafrol is used as the starting material and oxidized to the epoxide which is subjected to thermal or catalytic rearrangement (Hoering, Ber. Dt. Chem. Ges. 38, 2296–99; idem. 3464–3488 (1905)), and the resulting piperonyl methyl ketone is reduced to the corresponding alcohol.

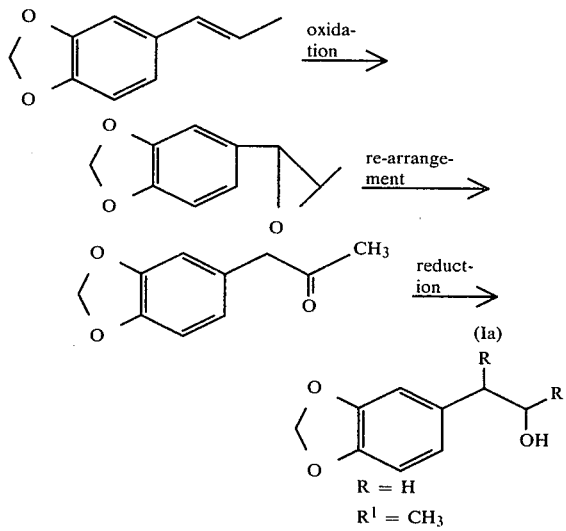

The aldehydes of the formula (Ib) also to be used as starting material are known. The following may be mentioned as examples: formaldehyde, acetaldehyde, propionaldehyde, butyraldehyde and isobutyraldehyde.

The process for the preparation of the compounds according to the invention is optionally carried out using a suitable diluent. Virtually any inert organic solvent can be used for this purpose, especially aliphatic and aromatic, optionally chlorinated hydrocarbons such as benzene, chlorobenzene, dichlorobenzene, toluene, xylene, methylene chloride, ethylene chloride, chloroform and carbon tetrachloride.

The process according to the invention is in general carried out using an acidic catalyst. Preferably, (gaseous) hydrogen chloride is used for this purpose.

The reaction temperature can be varied within a substantial range. In general, the reaction is carried out at about 0° to 80° C., preferably at about 10° to 50° C. The reaction is in general carried out under normal pressure.

In carrying out the process according to the invention, about 1.0 to 1.5, preferably about 1.1 to 1.3, mols of aldehyde of the formula (Ib) are in general employed per mol of hydroxy-alkylbenzodioxole derivative of the formula (Ia). In general, the components are introduced into one of the stated diluents and are stirred for several hours at the stated temperatures, while passing hydrogen chloride through the mixture. Working up is effected by washing with water, drying the organic phase and stripping off the solvent in vacuo. The crude products thus obtained can be purified by vacuum distillation or recrystallization. They are characterized by the melting point.

As already mentioned, combinations of the isochromane derivatives according to the invention with carbamates, carboxylic acid esters, phosphoric acid esters and halogenoalkanes exhibit an outstanding increase in action compared to the individual active compounds and compared to the sum of their actions.

The weight ratios of the groups of active compounds can vary within relatively wide ranges. In general, the isochromane component (1) is employed together with the remaining active compounds in component (2) in a ratio of about 0.1:10 to 10:0.1. However, ratios, in the mixture, of about 0.5:1.0 to 3.0:1.0 have proved particularly suitable.

The active compound combinations are well tolerated by plants, have a favorable level of toxicity to warm-blooded animals, and can be used for combating arthropod pests, especially insects and acarids, which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Dipolopoda, for example *Blaniulus guttulatus;* from the class of the Chilopoda, for example *Geophilus carpophagus* and *Scutigera* spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticultiermes spp.;

from the order of the Anoplura, for example *Phylloxera vastatrix*, Pemphigus spp., *Pediculus humanus corporis*, Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci*;

from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae*, Myzus spp.., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Laphygma exigua, Mamestra brassicae, Panolis flammea, Prodenia litura*, Spodoptera spp., *Trichoplusia ni, Carpocapsa pomonella*, Pieris spp., Chilo spp., *Pyrausta nubilalis, Ephestia keuhniella, Galleria mellonella, Cacoecia podana, Capua reticulana, Choristoneura fumiferana, Clysia ambiguella, Homona magnanima* and *Tortrix viridana*;

from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae*, Diabrotica spp., *Psylliodes chrysocephala, Epilachna varivestia*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus holoeucus, Gibbium psylloides*, Tribolium spp., *Tenebrio molitor*, Agriotes spp., Conoderus spp., *Melolontha melolontha, Amphimallon solstitialis* and *Costelytra zealandica*;

from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster*, Musca spp., Fannia spp., *Calliphora erythrocephala*, Lucilia spp., Chrysomyia spp., Cuterebgra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*;

from the order of the Siphonaptera, for example *Xenopsylla cheopis* and Ceratophyllus spp.;

from the class of the Arachnida, for example *Scorpio maurus* and *Latrodectus mactans*;

from the order of the Acarina, for example *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin suphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

Furthermore, the invention provides crops protected from damage by arthropods by being grown in areas in which immediately prior to and/or during the time of the growing a composition of the present invention was applied.

It will be seen that the usual methods of providing a harvested crop may be improved by the present invention.

PREPARATIVE EXAMPLES

Example 1:

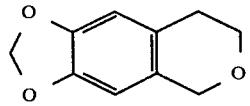
(1)

Hydrogen chloride was passed into a mixture of 57 g (0.34 mol) of 4-(2-hydroxy-ethyl)-1,2-methylenedioxybenzene, 12.8 g (0.45 mol) of formaldehyde and 200 ml of ethylene chloride, while cooling at 20° C., until a clear solution had formed. The solution was stirred for 6 hours at 40° C. while passing hydrogen chloride through it, and was then stirred overnight at room temperature, washed with water and sodium bicarbonate solution and dried. After stripping off the solvent in vacuo, the crude product which remained was purified by vacuum distillation. Yield 38 g (63% of theory), boiling point 122° C./3 mm Hg. The product crystallized after trituration with ether/petroleum ether; melting point 87° C.

Example 2

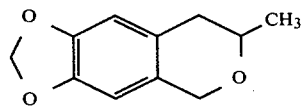
(2)

Hydrogen chloride was passed into a mixture of 90 g (0.5 mol) of 4-(2-hydroxy-n-propyl)-1,2-methylenedioxybenzene, 18.8 g (0.625 mol) of formaldehyde and 250 ml of ethylene chloride at 15° to 20° C., until a clear solution had formed. The solution was stirred for 6 hours at 40° to 45° C., left to stand overnight, poured into ice-water, washed with water and sodium bicarbonate solution and dried. The solvent was distilled in vacuo and the crude product was purified by vacuum distillation.

Yield 41 g (43% of theory), boiling point 136° C./3 mm Hg. The product crystallized after trituration with ether/petroleum ether; melting point 73° C.

The activity of the compounds of this invention is illustrated by the following example:

Example 3

$LT_{100}$ test

Test insects: *Musca domestica*, Weymanns strain (resistant to carbamates and phosphoric acid esters)
Solvent: Acetone Solutions were prepared from the active compounds, synergistic agents and mixtures of active compounds and synergistic agents, and 2.5 ml of the solutions were pipetted onto filter paper discs of 9.5 cm diameter in Petri dishes. The filter paper adsorbed the solutions. The Petri dishes were left standing open until the solvent had completely evaporated. 25 test insects were then introduced into the Petri dishes, and the dishes were covered with a glass lid.

The condition of the test insects was checked continuously for up to 6 hours. The time required for a 100% knock-down action was determined. If the $LT_{100}$ was not reached after 6 hours, the percentage of the test animal which had been knocked down was determined.

In this test, the compounds of Examples 1 and 2 exhibited a superior action compared with the prior art.

It will be appreciated that the instant specification and examples are set forth by way of illustration and not limitation, and that various modifications and changes may be made without departing from the spirit and scope of the present invention.

What we claim is:

1. An arthropodicidal composition containing as active ingredients an anthropodicidally effective amount of (1) at least one compound of the formula

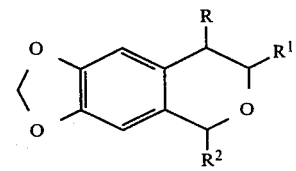

in which R, $R^1$ and $R^2$ each independently is hydrogen or alkyl, and (2) at least one compound selected from the group consisting of (A) carbamates, (B) carboxylic acid esters, (C) phosphoric acid esters and (D) halogenoalkanes.

2. A composition according to claim 1, wherein the weight ratio of component (1) to component (2) is from about 0.1:10 to 10:0.1.

3. A method of combating arthropods which comprises applying to the arthropods, or to a habitat thereof, an arthropodicidally effective amount of a composition according to claim 1.

4. The method according to claim 3 wherein component (A) is
6,7-methylenedioxy-isochromane or
3-methyl-6,7-methylenedioxy-isochromane.

* * * * *